United States Patent [19]

Gallagher

[11] Patent Number: 5,023,560
[45] Date of Patent: Jun. 11, 1991

[54] DEVICE FOR MOISTURE MEASUREMENT OF PARTICULATE MATERIAL

[76] Inventor: John G. Gallagher, 77 Town Street, Old Malton, Malton, North Yorkshire, England

[21] Appl. No.: 470,846

[22] Filed: Jan. 26, 1990

[51] Int. Cl.$^5$ ............................................. G01R 27/26
[52] U.S. Cl. .................................... 324/664; 340/602; 324/690
[58] Field of Search ............... 324/664, 668, 682, 686, 324/689, 690, 708, 724; 340/602; 73/336.5

[56] References Cited

U.S. PATENT DOCUMENTS

| | | | |
|---|---|---|---|
| 2,920,272 | 1/1960 | Erdman et al. | 324/668 |
| 3,252,086 | 5/1966 | Lundstrom | 324/668 |
| 3,581,197 | 5/1971 | Morey, Jr. et al. | 324/689 |
| 3,882,383 | 5/1975 | Matlin . | |
| 3,968,428 | 7/1976 | Numoto . | |
| 4,044,607 | 8/1977 | Deal | 324/668 |
| 4,228,393 | 10/1980 | Pile | 324/668 |
| 4,259,632 | 3/1981 | Ahtiainen | 324/664 |
| 4,399,404 | 8/1983 | Resh | 324/689 |

FOREIGN PATENT DOCUMENTS

| | | |
|---|---|---|
| 922225 | 3/1963 | United Kingdom . |
| 1297156 | 11/1972 | United Kingdom . |
| 2132767 | 7/1984 | United Kingdom . |

*Primary Examiner*—Kenneth Wieder
*Assistant Examiner*—Maura K. Regan
*Attorney, Agent, or Firm*—McCubbrey, Bartels, Meyer & Ward

[57] ABSTRACT

A device for measurement of moisture in a body of particulate material, such as a grain in a pile or in a silo, is in the form of a spear with a set of conductive plates 2 carried at one end of a shaft 1 for immersion in the body of particulate material, and a read out meter 4 and carrying handle 3 at the other end of the shaft. Normally the set of conductive plates measure capacitance of the material via a phase locked loop oscillatory circuit. The plates are disposed and shaped to facilitate entry into and removal from the body of particulate material.

10 Claims, 2 Drawing Sheets

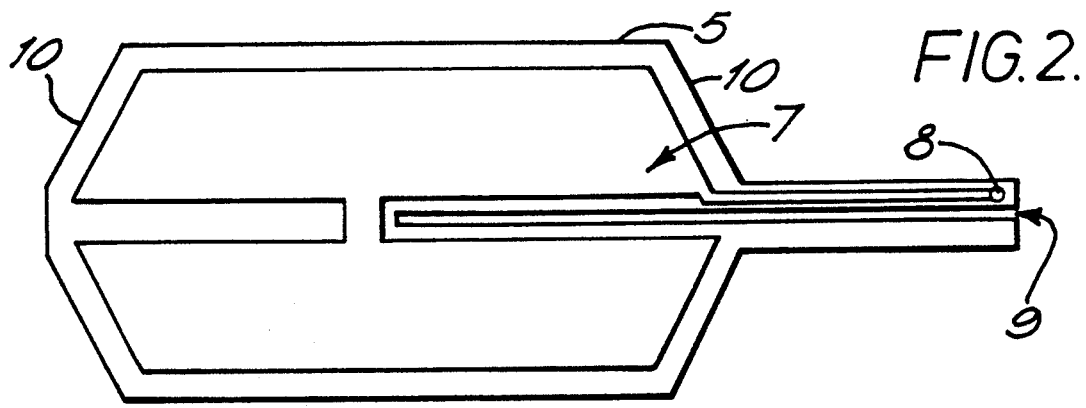
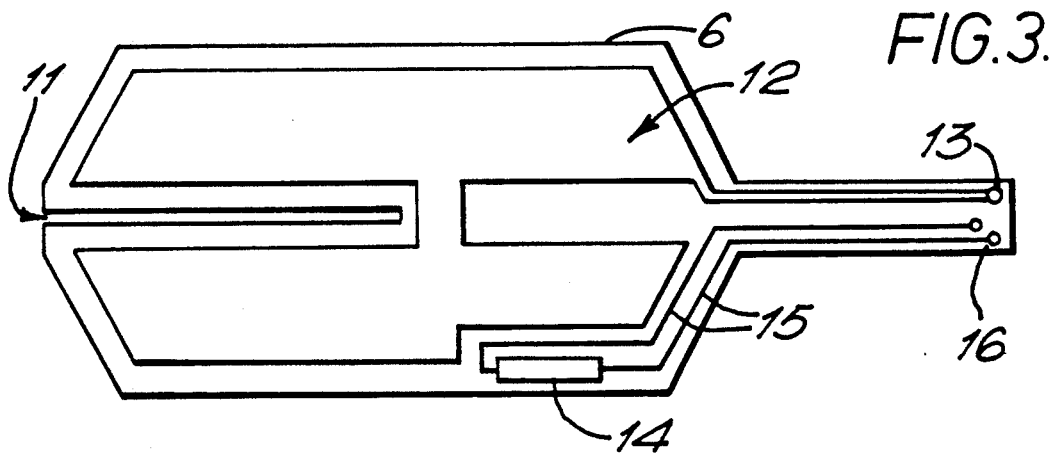
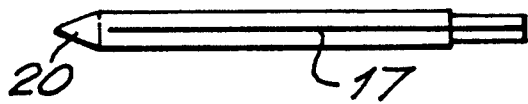
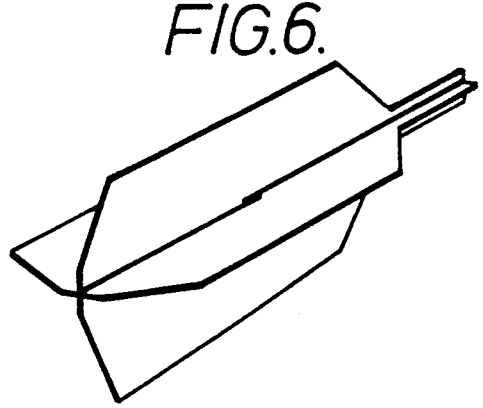
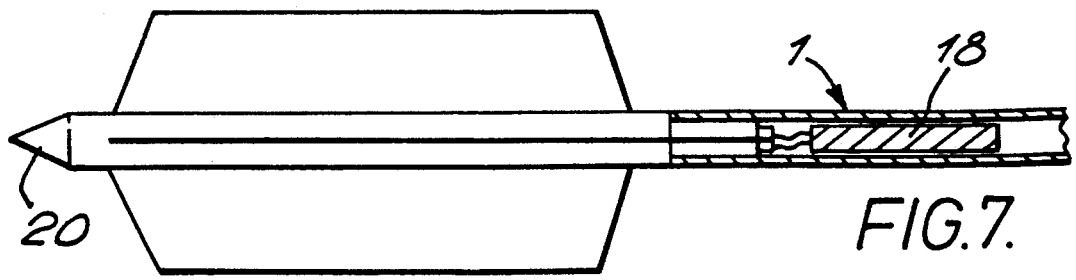

DEVICE FOR MOISTURE MEASUREMENT OF PARTICULATE MATERIAL

BACKGROUND OF THE INVENTION

The present invention relates to the measurement of moisture within a body of particulate material, for example a pile or silo of cereal grain.

Such bodies of material often contain a quantity of water. The weight and/or quality of the material will depend on its moisture content. It may therefore be desirable to know the moisture content of the body of material in order to provide, for example, a fair and consistent evaluation of the weight of the material.

For greatest accuracy, the present invention aims to measure the moisture content at a point well within a body of particulate material. At the surface of such a body the moisture content is likely to be reduced by contact of the material with the surrounding atmosphere and the consequent evaporation of the moisture.

SUMMARY OF THE INVENTION

A preferred form of the invention is a device for measurement of moisture in a body of particulate material. The device includes a support shaft, at least two electrically conductive plates carried at an end region of the shaft and each disposed as fins extending lengthwise of the shaft, and means for measurement of an electrical property of the material between the plates in order to measure the moisture content of the particulate material when the plates are immersed in the body of the particulate material.

Preferably the electrical property to be measured is capacitance, but other properties such as resistance or conductance may alternatively be measured.

Since the plates are disposed lengthwise of the support shaft and parallel to the shaft, the plates can be pushed into the body of material for measurement of the electrical property at a point well within the body of material.

Preferably the device comprises four electrically conductive plates disposed successively at right angles around the shaft, and with diametrically opposed plates electrically connected together.

A practical arrangement is for each of the plates to be formed of a resilient tough plastics material having an electrically conductive surface formed as a printed circuit, for example a deposited and etched foil of copper on a carrier of phenolic resin or other circuit board material.

Preferably each electrically conductive plate is forwardly and rearwardly bevelled in order to facilitate movement of the shaft and plates into and out of the body of material.

The electrical capacitance measuring means may comprise a tuned circuit whose frequency is determined by the capacitance of the plates.

In one arrangement the tuned circuit forms part of an oscillator circuit which is arranged to be compared with a constant frequency reference oscillator and the frequency difference is arranged as a voltage for display of an output proportional to the capacitance of said electrically conductive plates.

In another form, the voltage necessary to bring the frequency of the two circuits into conformity is measured.

The oscillator circuit should preferably be arranged to operate at a frequency greater than 2 MHz since water becomes too lossy at frequencies below 1 MHz and measurement of capacitance below that frequency becomes unreliable.

An embodiment of the invention will now be described by way of example with reference to the accompanying drawings.

BRIEF DESCRIPTION OF THE DRAWINGS

FIGS. 2 and 3 are plan views of the electrically conductive plates;

FIGS. 4 and 5 show a shaft end piece;

FIG. 6 shows the plates in a part assembled condition;

FIG. 7 shows the end assembly of the shaft; and

DETAILED DESCRIPTION OF THE INVENTION

Figure 1:
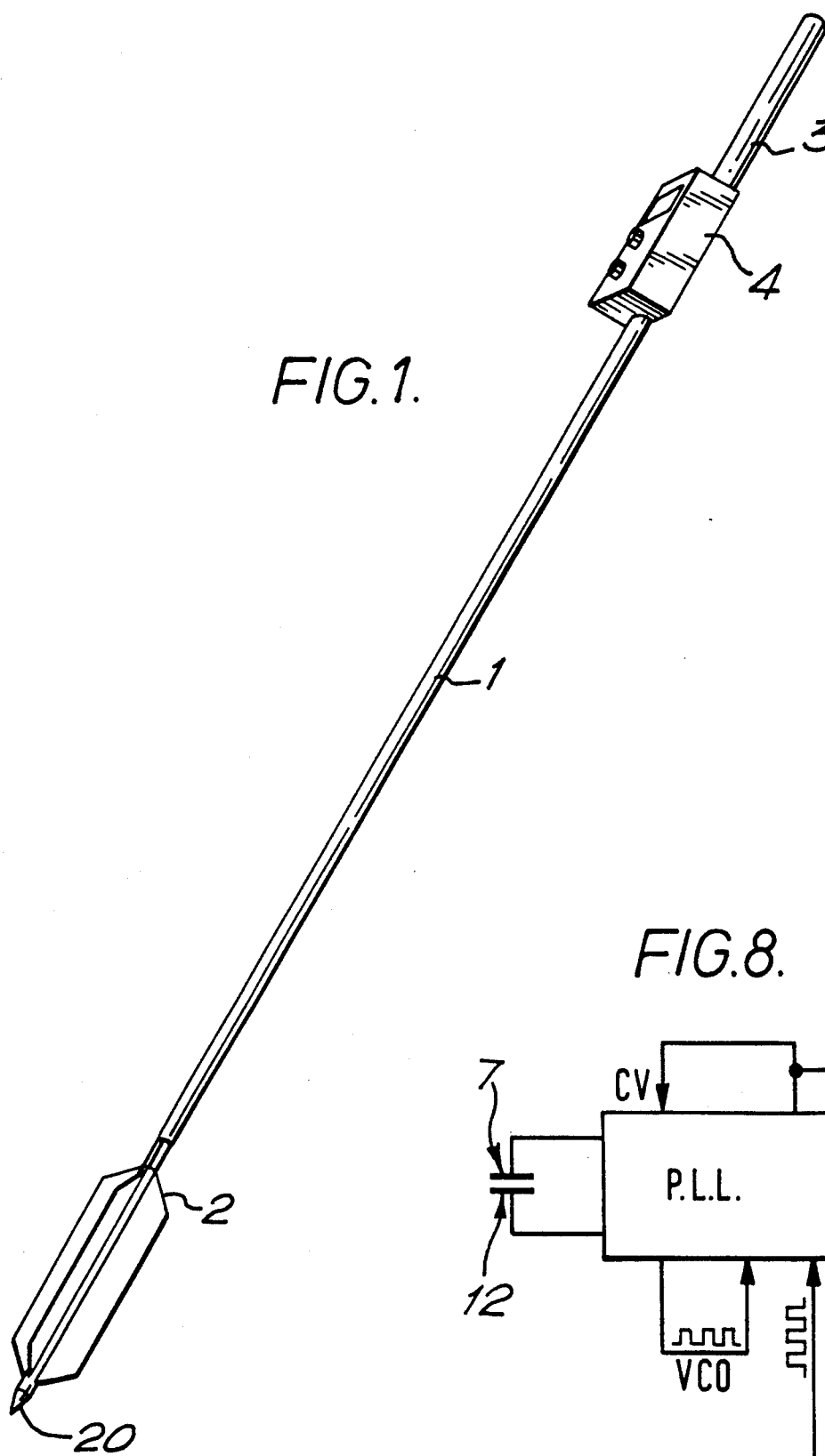
FIG. 1 is a perspective view of a moisture measurement device.

Referring first to FIG. 1, a preferred embodiment of the measurement device is in the form of a spear comprising a hollow metal shaft 1 carrying at one end a set of electrically conductive plates 2 and at its other end a carrying handle 3 and a readout meter 4. The plates each extend lengthwise of the shaft, in the manner of a fin. Each plate may be flat and lie in a respective plane including the axis of the shaft.

Referring now to FIGS. 2 and 3, the electrically conductive plates are formed of two pairs of slotted plates 5 and 6 of resilient plastics material such as phenolic resin or other circuit board material. The first of these pairs of plates 5 has a deposited copper foil element 7 which defines one plate of a capacitor. The copper foil leads out to a connection point 8.

The plate pair 5 has an axial slot 9 for interfitting accommodation of the other slotted pair of plates 6. The plates have bevelled edges 10 to facilitate movement of the instrument into and out of a bulk of particulate material.

The second pair of slotted plates 6 is similar in overall shape to the first pair of slotted plates 5 except in that it has a slot 11 in a different location whereby when the two pairs of plates are fitted together by means of slot 9 and slot 11 they are located in the position shown in FIG. 6; that is, like the assembled fins of a dart.

The pair of slotted plates 6 also has a deposition of a copper foil 12 which defines the other capacitor plate and which leads to a connection point 13. Also incorporated on the plate pair 6 is a platinum resistance thermometer 14 embedded within the material of the plastic support and having copper tracks 15 etched in the copper foil which lead to connection points 16.

The two plate pairs 5 and 6 are slotted together in the configuration shown in FIG. 6 and then slid into position within a split-ended PVC dowel 17 which also forms a pointed end 20 to the device. A longitudinal view of the dowel is shown in FIG. 4, and a cross-sectional view is shown in FIG. 5.

FIG. 7 shows the assembled arrangement of the plates, and the dowel piece 17 fits into the end of the hollow shaft of metal 1. The end connections 8 and 13 of the foils on the plates 7 and 12 are connected to a preamplifier circuit 18 located close to the plates within the hollow of the shaft 1. The circuit 18 then feeds a voltage output to the indicator device 4 as a measurement of the capacitance between the two foils 7 and 12.

Figure 8:
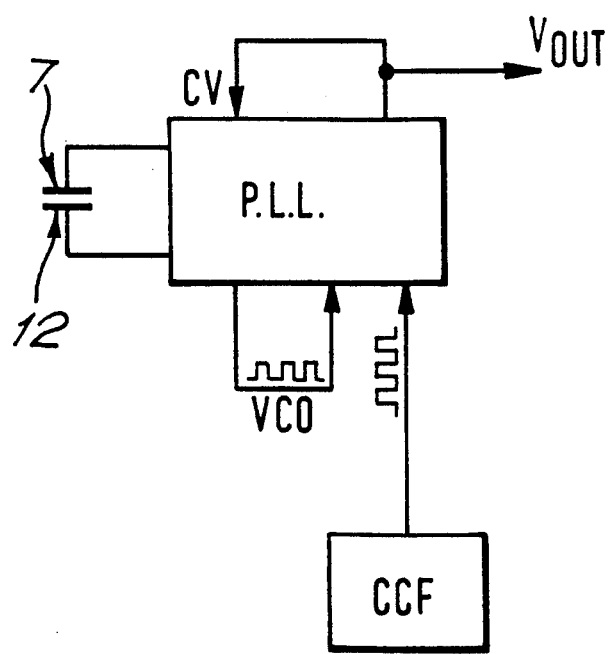
FIG. 8 is a circuit diagram for use with the described equipment.

FIG. 8 shows the circuit arrangement for creating the voltage for the indication of the value of the capacitance.

A voltage controlled oscillator has its frequency determined by the capacitance between the etched foils 7 and 12 on the plates 5 and 6.

A phased locked loop circuit then compares the output from the voltage controlled oscillator (VCO) with the output from a constant reference frequency provided by a constant clock frequency unit (CCF), and drives the voltage controlled oscillator to match the reference frequency.

If the capacitance changes, the VCO frequency changes correspondingly. In order to maintain the VCO frequency equal to the reference, the VCO control voltage (CV) changes proportionately in such a way that capacitance equals a constant multiplied by the VCO control voltage. Therefore by measuring the VCO control voltage, CV, the capacitance can be determined, and that voltage measurement will be proportional to the capacitance in a linear manner.

The output voltage $V_{OUT}$, with low pass filtration, is then displayed on the readout meter 4 as a measure of moisture content of the particulate material. The scale may be calibrated for the various different kinds of material to be encountered such as wheat, barley, oats, rape, peas or beans, for example.

What is claimed is:

1. A device for measurement of moisture in a body of particulate material, comprising a support shaft having an end region, at least two electrically conductive plates carried at the end region of said shaft and each configured as a fin for contact with said particulate material, each said fin extending lengthwise of said shaft, and means for measurement of an electrical property of the material between said plates in order to measure the moisture content of the particulate material when said plates are immersed in said body of the particulate material.

2. The device of claim 1 in which the electrical property is capacitance.

3. The device of claim 2 in which the electrical property measurement means comprises an oscillator circuit having a variable frequency which is dependent on the capacitance between said plates and in which the electrical property measurement means further comprises a constant frequency reference oscillator circuit, and means for comparison of the said variable frequency and said constant frequency.

4. The device of claim 1 in which each plate is forwardly and rearwardly bevelled in order to facilitate movement of said shaft and plates into and out of the body of material.

5. A device for measurement of moisture in a body of particulate material, comprising a support shaft having an end region, four electrically conductive plates carried at the end region of said shaft and each disposed in a plane parallel to said shaft and successively at right angles around said shaft, with diametrically opposed plates connected together, and means for measurement of an electrical property of the material between said plates in order to measure the moisture content of the particulate material when said plates are immersed in said body of the particulate material.

6. The device of claim 5 in which each plate is formed from a printed circuit carrier material having a copper foil layer etched thereon.

7. A device for measurement of moisture in a body of particulate material, comprising a shaft having first and second end regions, a plurality of pairs of electrically conductive plates each disposed as a fin for exposure to said material at the said first end region of said shaft, the fins in each pair being electrically connected, whereby said pairs form a capacitative sensing means, electrical circuit means for measurement of the capacitance of the capacitative sensing means in order to measure the moisture content of the particulate material when said plates are immersed in said body of the particulate material, and an indicator for said moisture content, said indicator being electrically coupled to said circuit means and disposed near said second end region.

8. The device of claim 7 in which each plate is forwardly and rearwardly bevelled in order to facilitate movement of said shaft and plates into and out of the body of material.

9. The device of claim 7 in which each plate comprises a printed circuit carrier material having a copper foil layer etched thereon.

10. A device of for measurement of moisture in a body of particulate material, comprising a support shaft having an end region, four electrically conductive plates disposed as longitudinal fins at the end region of said shaft, and spaced at ninety degree intervals about said shaft, means connecting each pair of diametrically opposed plates together to form a capacitative sensing means and electrical means for measurement of the capacitance of the capacitative sensing means in order to measure the moisture content of the particulate material when said plates are immersed in said body of the particulate material.

* * * * *